Figure 1:
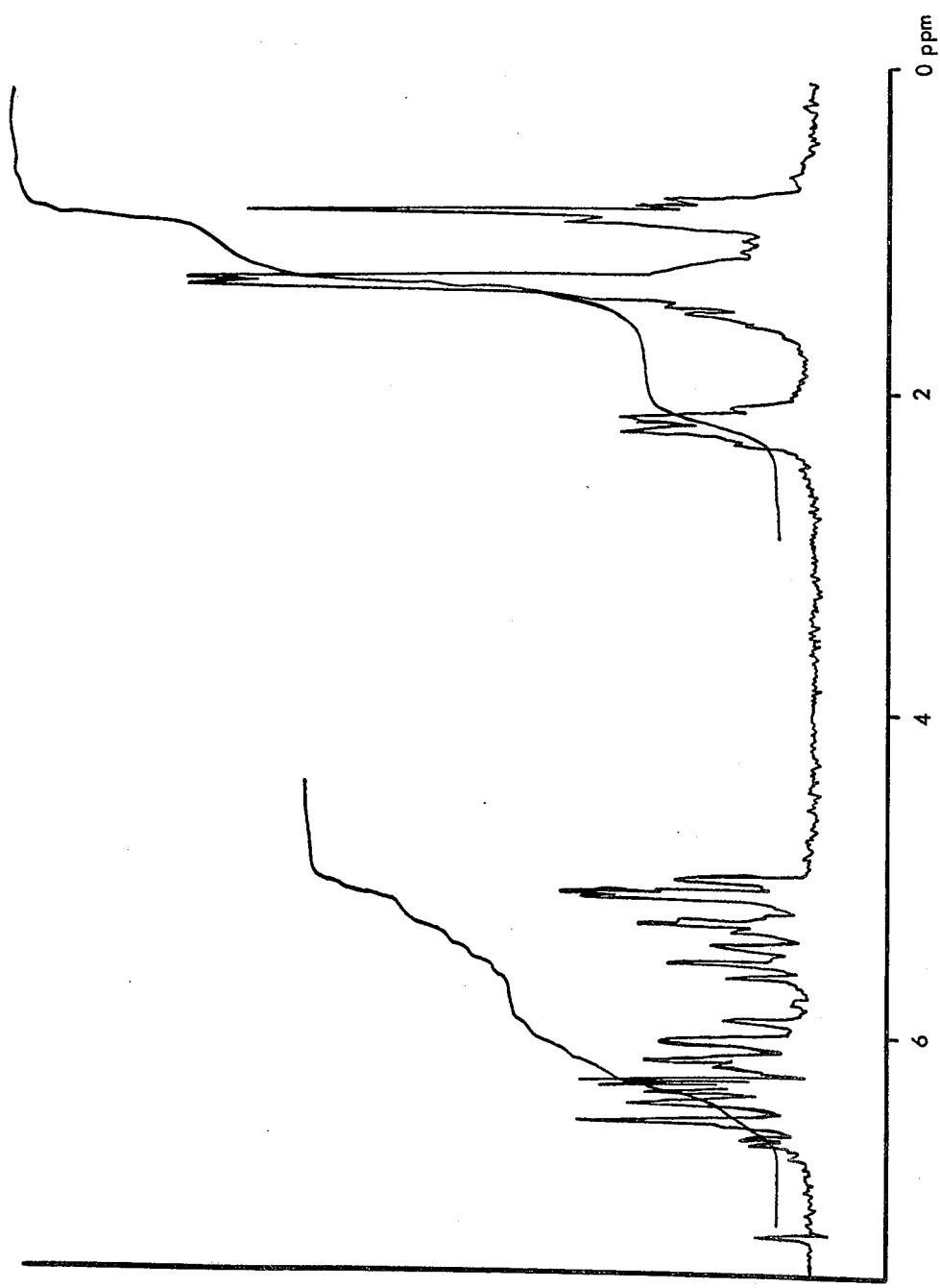
Figure 2:
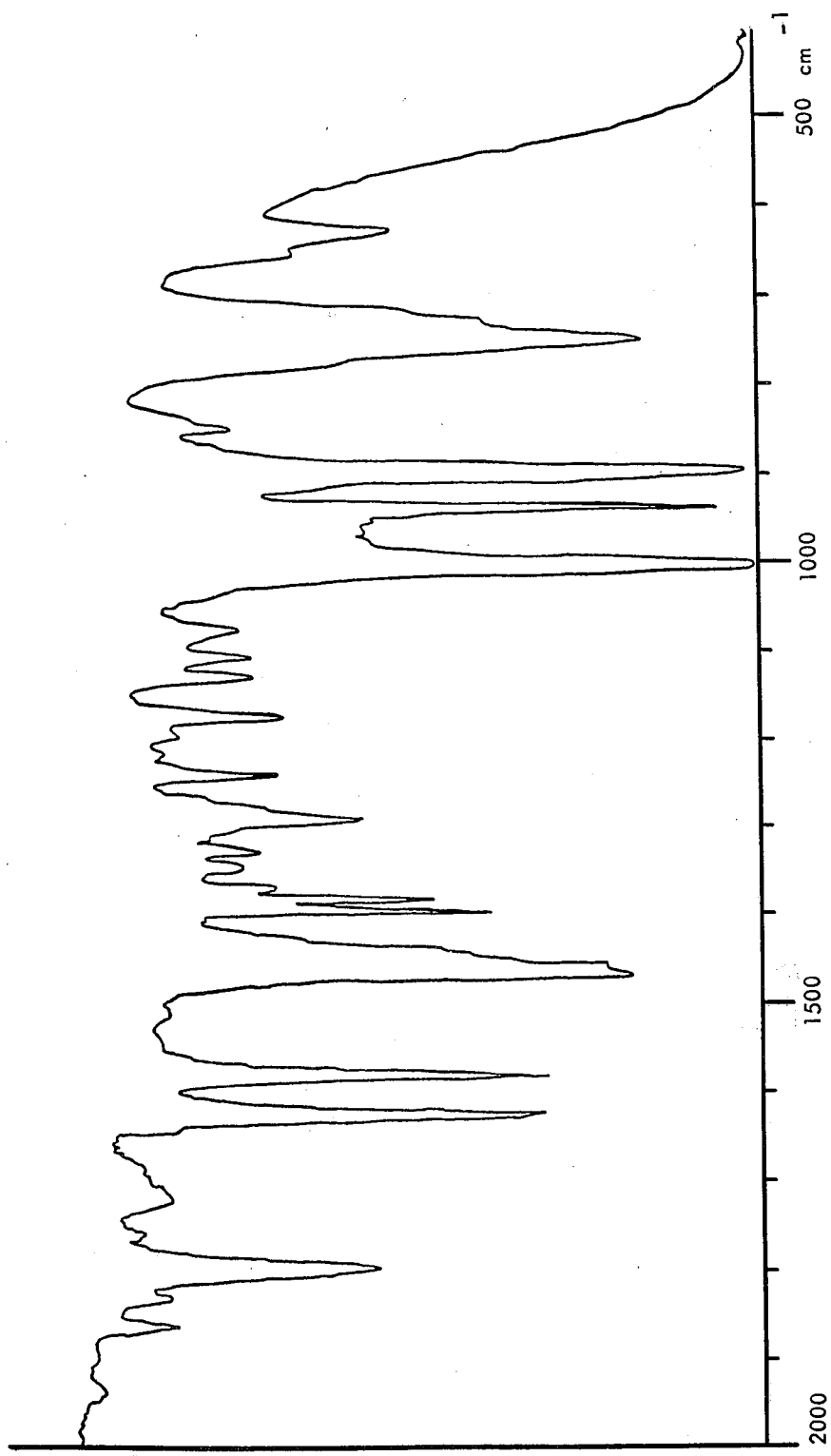
Figure 3:
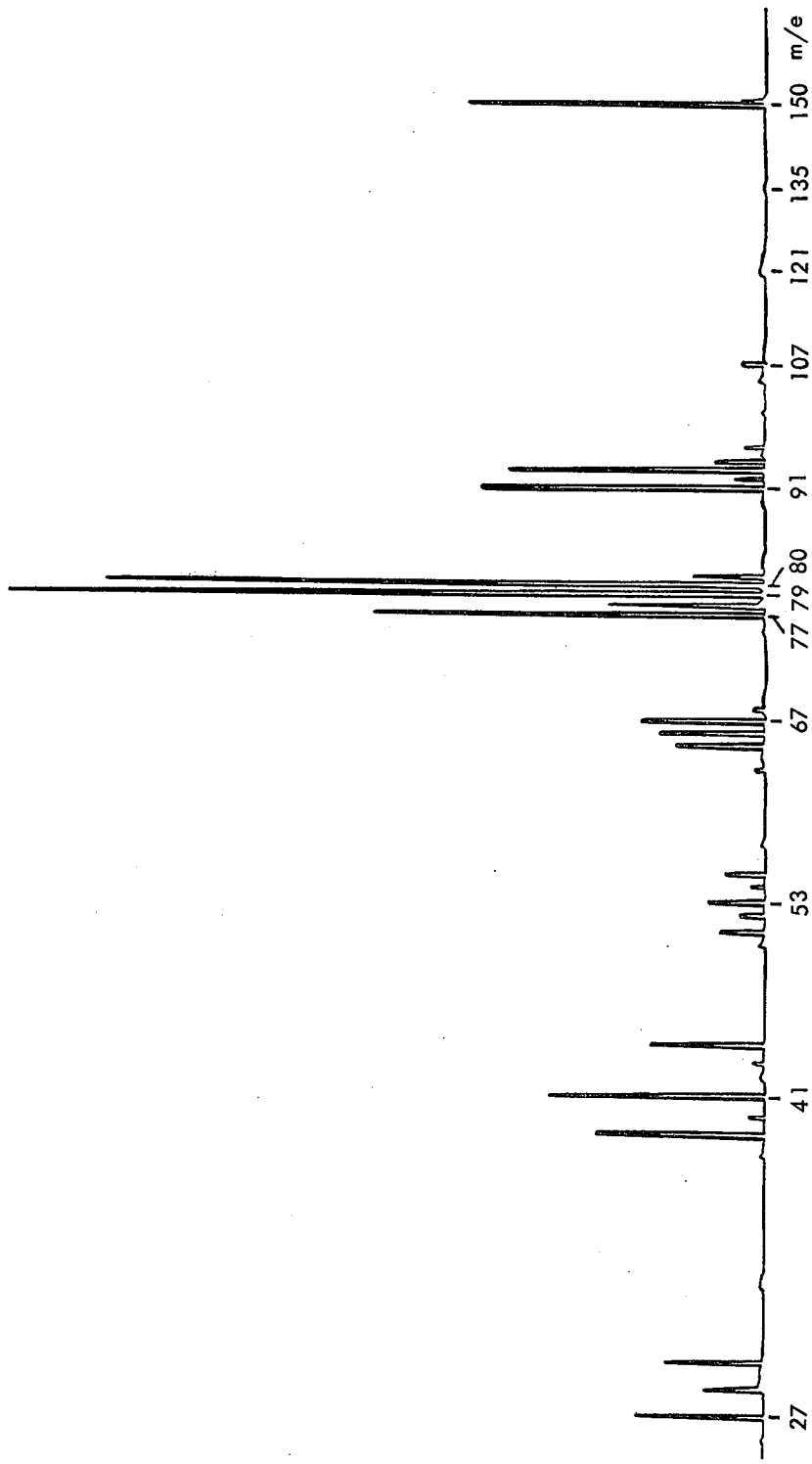
Figure 4:
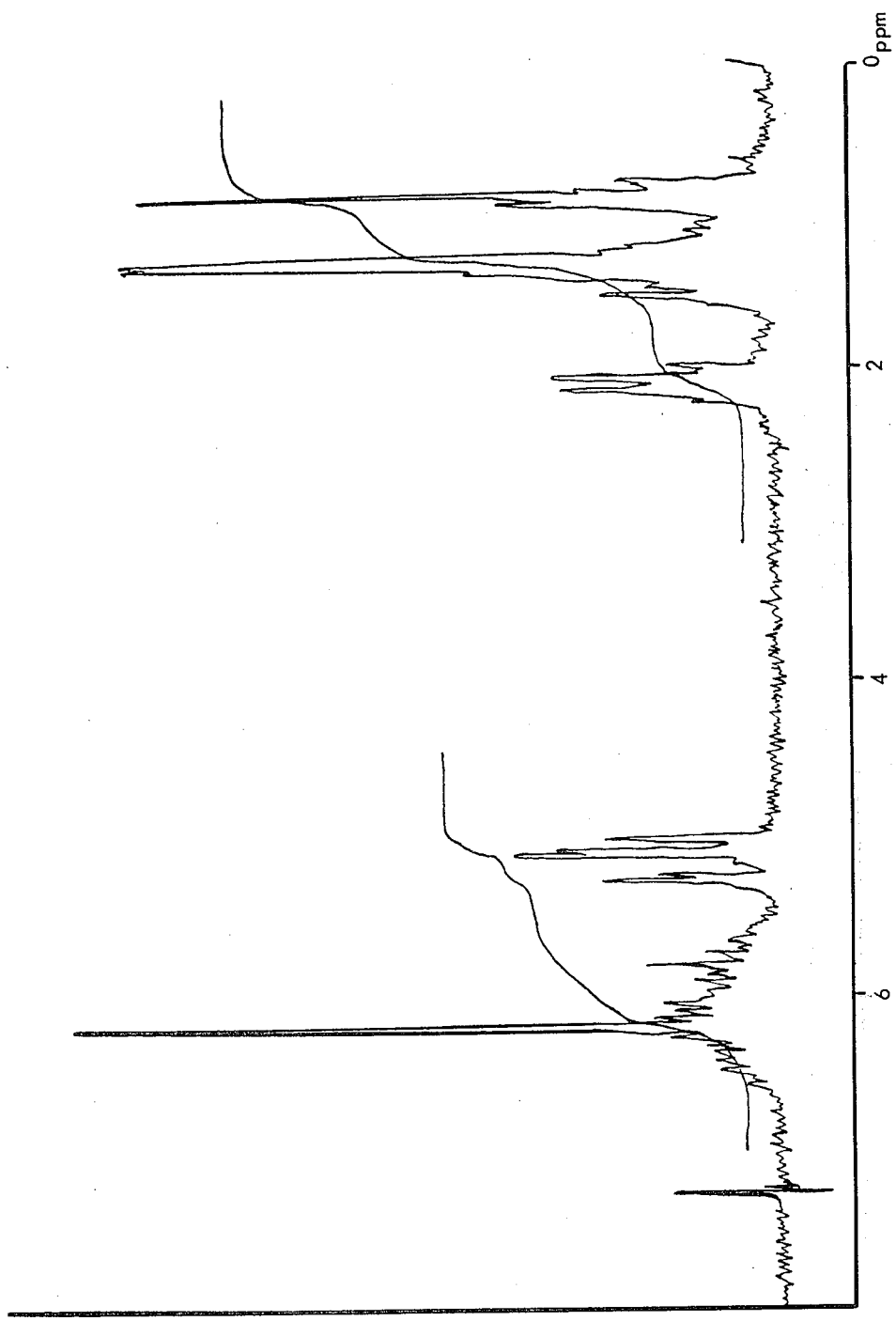
Figure 5:
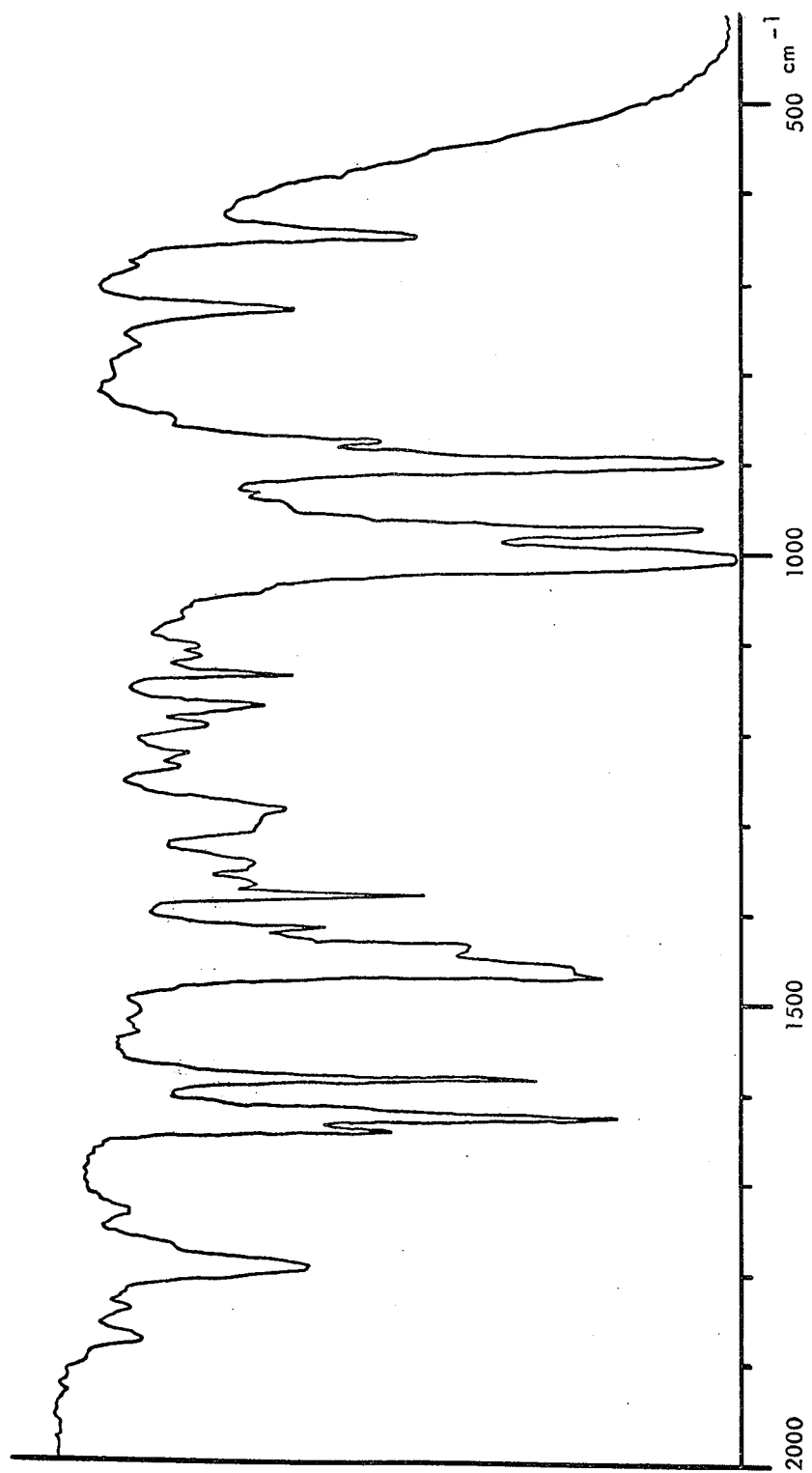

United States Patent [19]
Näf et al.

[11] 4,014,951
[45] Mar. 29, 1977

[54] PROCESS FOR THE PREPARATION OF POLY-UNSATURATED HYDROCARBONS

[75] Inventors: Ferdinand Näf, Geneva; Günther Ohloff, Bernex-Geneva; Albert Eschenmoser, Kusnacht, all of Switzerland

[73] Assignee: Firmenich S.A., Geneva, Switzerland

[22] Filed: Jan. 28, 1976

[21] Appl. No.: 653,245

Related U.S. Application Data

[62] Division of Ser. No. 473,087, May 24, 1974, Pat. No. 3,960,977.

[30] Foreign Application Priority Data

June 7, 1973  Switzerland ............... 8247/73

[52] U.S. Cl. .......................................... 260/677 R
[51] Int. Cl.² ....................................... C07C 11/21
[58] Field of Search ........................ 260/677 R

[56] References Cited
UNITED STATES PATENTS

| | | | |
|---|---|---|---|
| 2,842,599 | 7/1958 | Isler et al. | 260/677 R |
| 3,344,202 | 9/1967 | Ziegenhain | 260/677 R |
| 3,532,762 | 10/1970 | Corbier et al. | 260/677 R |

*Primary Examiner*—Herbert Levine
*Attorney, Agent, or Firm*—Pennie & Edmonds

[57] ABSTRACT

Process for the preparation of poly-unsaturated hydrocarbons, in particular undeca-1,3,5-triene, which comprises reacting a quaternary phosphonium salt with hexanal.

The product obtained in accordance with the process of the invention is a useful perfuming ingredient.

10 Claims, 6 Drawing Figures

PROCESS FOR THE PREPARATION OF POLY-UNSATURATED HYDROCARBONS

This is a division of application Ser. No. 473,087, filed May 24, 1974, now U.S. Pat. No. 3,960,977.

BACKGROUND OF THE INVENTION

In the course of certain investigations undertaken by different research groups relative to the study of the constituents of natural galbanum essential oil, it becomes apparent that this essential oil contains certain non-terpenic hydrocarbons, in particular, undeca-1,3,5-triene.

This compound may occur under the form of one of the geometrical isomers of formula

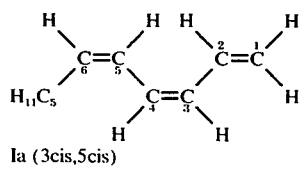
Ia (3cis,5cis)

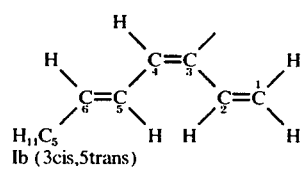
Ib (3cis,5trans)

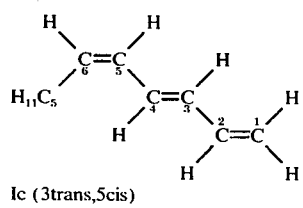
Ic (3trans,5cis)

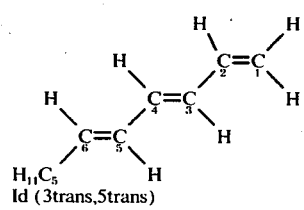
Id (3trans,5trans)

A hydrocarbon with a non-terpenic skeleton and a very powerful odour was in fact isolated by Y. Chrétien-Bessière et al. from galbanum essential oil [cf.: Bull. Soc. Chim. France, 97 (1967)]. This investigation allowed assigning the structure of undeca-1,3,5-triene to the compound in question and to determine that it possessed a double bond with cis isomerism and a double bond with trans isomerism; however, the respective position of these double bonds in the molecule could not be determined. In a subsequent communication, Y.R. Naves [cf.: Bull. Soc. Chim. France, 3152 (1967)] confirmed the presence of undeca-1,3,5-triene in galbanum essential oil and assigned, by making use of a deep spectral analysis, the structure of the two isomers of the product in question, these isomers having been defined as the compounds of formula Ic and Id. However, these two compounds could not be isolated in their pure state. In fact, in an attempt to separate them by means of spinning band distillation columns, an easy dimerization of the compounds occurred. A separation by means of vapour phase chromatography or low temperature crystallization proved to be equally unsuccessful.

The finding that the product isolated from the hydrocarbons fraction of galbanum essential oil was essentially consisting of a mixture of two geometrical isomers of undeca-1,3,5-triene, was later confirmed by a study published subsequently by P. Teisseire et al. [cf.: Recherche, 16, 5 (1967)]. However, contrary to the results obtained by the previous authors, this latter publication discloses the presence in the galbanum essential oil of two hydrocarbon isomers defined as undeca-1,3 cis,5-cis-triene and undeca-1,3cis,5trans-triene. The former of these compounds was considered to be, by the authors of this article, the odour principle of the essential oil [cf. also: Swiss Pat. No. 496,084].

The prior art, therefore, discourages the possibility of isolating and using as perfuming ingredients undeca-1,3trans, 5cis-triene and undeca-1,3trans,5trans-triene.

It has now been surprisingly found that the characteristic odour of galbanum essential oil is mainly conferred by the presence therein of undeca-1,3trans,5cis-triene (compound Ic). Though less developed, the odoriferous characters of the other isomer, undeca-1,3trans,5trans-triene (compound Id), present, nevertheless, a great interest for the perfumers. Consequently, the cited pure compounds find a useful industrial application on their own or in the form of mixtures of thir geometrical isomers.

Galbanum essential oil develops a characteristic and particularly powerful odoriferous note of green type with a tonality reminiscent of dry wood of balsamic character [cf.: S. Arctander, "Perfume and Flavor Materials of Natural Origin", N.Y. USA (1960)]. Although it is used at small concentrations, this essential oil is particularly suitable, namely as ingredient in floral type compositions, such as for instance hyacinth, violet, narcissus, lavender or gardenia type compositions, wherein its "leaf" undertone develops or enhances the natural character.

THE INVENTION

This invention relates to a process for the preparation of undeca-1,3trans,5cis-triene and/or undeca-1,3trans, 5trans-triene, which comprises reacting a quaternary phosphonium salt of formula

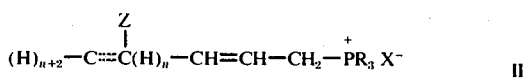
II wherein symbol R represents an aliphatic, cycloaliphatic or aromatic radical and X represents a halogen atom, such as chlorine, bromine or iodine, or a group such as $BF_4$ or $ClO_4$, and wherein:

a. index $n$ stands for 1, Z represents a halogen atom and the dotted lines define a single bond; or b. index $n$ stands for zero, Z represents a hydrogen atom and the dotted lines define a double bond, with hexanal, and subsequently separating, if so desired, the pure geometrical isomers.

The quaternary phosphonium salt of formula II, used as starting material in the process of the invention, can be synthetized according to one of the processes illustrated by the following reaction schemes:

A:

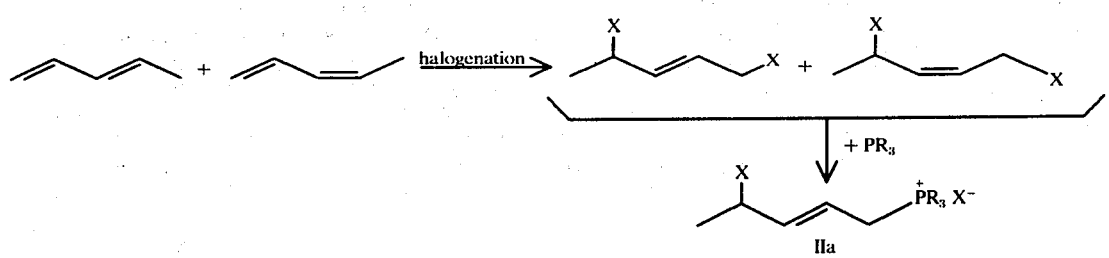

B:

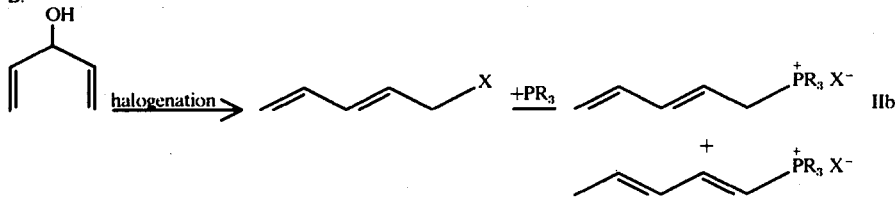

In the hereinabove schemes symbol R represents an aliphatic, cycloaliphatic or aromatic radical and X represents a halogen atom. The mixture of isomers of penta-2,4-diene, used as starting material in the method illustrated by scheme A above, is a commercially available compound which can be directly halogenated according to the method described in Ann. Chimie (Paris), 10, 377 (1928), to yield a dihalo-pent-2-ene derivative. The subsequent reaction step can be effected in accordance with the techniques currently used in the art for the preparation of a phosphonium salt [cf. e.g.: H.O. House, Modern Synthetic Reactions, Benjamin Inc., New York; R.F. Hudson, Structure and Mechanism in Organo-Phosphorous Chemistry, Academic Press, London (1965)].

Equally, penta-1,4-dien-3-ol [see scheme B hereinabove] is a commercial product [Fluka A.G., Buchs/SG, Switzerland], and its conversion to 1-halo-penta-2,4-diene can be carried out in accordance with the synthetic method described in Ann. Chimie, 7, 445 (1962).

According to an embodiment of the invention, the reaction between the quaternary phosphonium salt of formula II and hexanal is effected in the presence of a basic agent in accordance with the procedure followed for the Wittig type reactions [cf.: H.O. House, op. cit.]. Thus, for instance, in the case of a phosphonium salt of formula II*b*, suitable basic agents include an alkali metal hydride such as sodium or potassium hydride, an alkali metal alkoxide such as ethoxide, methoxide or ter-butoxide of sodium or potassium, or a mixed basic agent such as the product formed by the reaction between an alkyl derivative of an alkali metal and a secondary amine. Suitable alkali metals include lithium, sodium, potassium and their alloys, and secondary amines such as diethylamine, diisopropylamine, piperidine, diisobutylamine and ethyl-terbutylamine can be used. A preferred mixed basic agent is represented by the product of reaction between butyl-lithium and diisopropylamine. In this latter case the reaction between hexanal and the quaternary phosphonium salt of formula II*b* can be effected in the supplemental presence of a base, e.g. potassium ter-butoxide. As basic agent it is also possible to use an alkyl or aryl derivative of an alkali metal salt, e.g. phenyl-, butyl- or n-propyl-lithium. Butyl-lithium is preferred.

When a quaternary phosphonium salt of formula II*a* is used as starting material, it is preferred to use a strong base having a sterically hindered reactive centre. To this effect tertiary alkoxides or secondary amides, e.g. diisopropylamide or cyclohexylisopropylamide, of an alkali metal may be conveniently used.

The reaction which characterizes the process of the present invention can be carried out in an inert organic medium. Thus, preferential organic solvents include ethers, for instance diethylether, dioxan, tetrahydrofuran and dimethoxyethane, amides such as dimethylformamide, or dimethylsulphoxide. Mixtures of at least two of the said solvents can equally be used. The reaction conditions of temperature will depend upon a variety of factors including the time of the reaction, the particular reactants used and the solvents employed. Generally, however, the reaction is effected at a temperature comprised in between about 10° and 60° C. Variations from these temperatures are permissible, but for reasons of economy the reaction is carried out at room temperature.

In accordance with a preferred embodiment, the reaction is conducted at atmospheric pressure by admixing the reactants in an inert atmosphere, of argon or nitrogen for example.

Hexanal, equally used as starting material in the process of the invention, is a cheap commercial compound available in large quantities. The above described process of the invention presents a great industrial interest. It enables in fact to synthetize, in a limited number of reaction steps and with good yields, a mixture of undeca-1,3trans,5cis-triene and undeca-1,3trans,5trans-triene, the respective proportions of which are particularly suitable for a direct use of the said mixture for most of the practical industrial applications in the field of flavours and fragrances.

The concentrations of the two geometrical isomers in the mixture obtained by the process of the invention vary within large limits, but they are typically comprised in between about 30 and 70 % by weight of the total weight of the mixture. Thus, for instance, it is possible to obtain mixtures comprising about 30:70, 40:60 or 50:50 parts by weight of undeca-1,3trans,5cis-triene and undeca-1,3trans, 5trans-triene, respectively.

The said isomers can be separated one from the other by preparative vapour phase chromatography, particularly by using a column of the type Sp 1000, 4 mm × 2.5 m at a temperature of 155° C.

In the course of one of the above cited investigations on galbanum oil, Teisseire et al. [cf. op. cit.] attempted to prepare isomer Ic by a stereospecific synthesis, however, this compound was not isolated in its pure form. The same author achieved the synthesis of isomer Ic. The synthetic routes followed for these syntheses are illustrated hereinbelow.

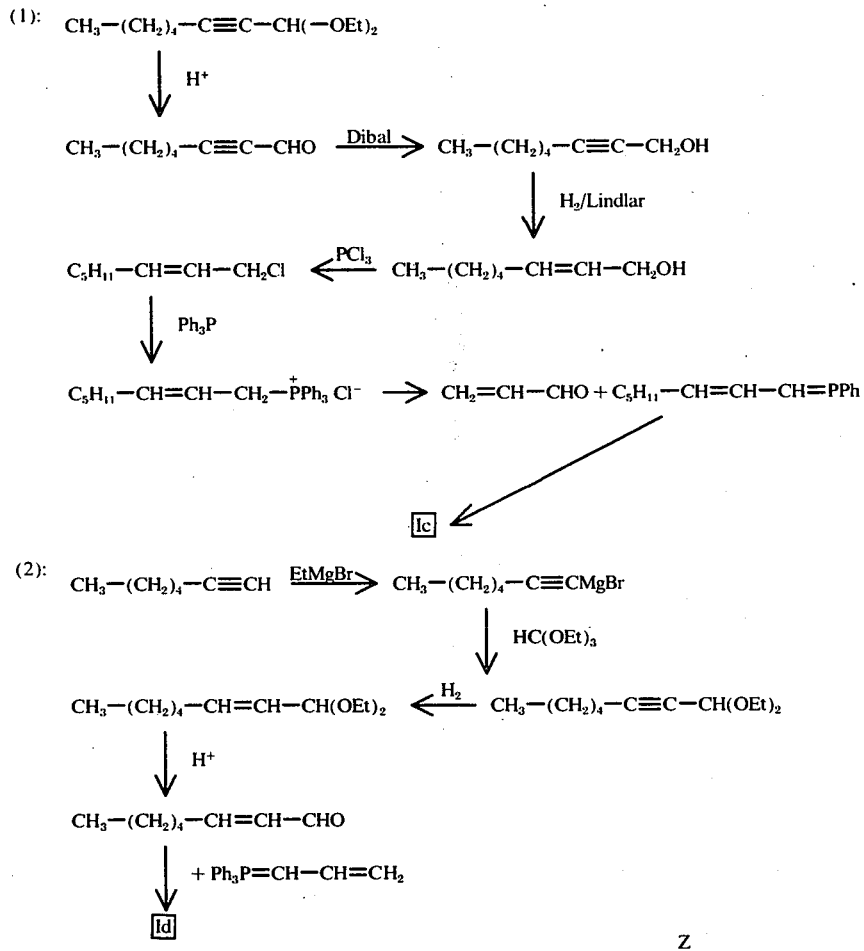

These syntheses afforded the desired compounds in very low yields and had the disadvantage that the starting material used, hept-1-yne, is a product available on the market only at high price. Therefore, the prior art hereinabove described processes possess only an academic interest.

In view of the selectivity of the reactions which characterize the process of the invention, it is now possible for the first time to put to the disposal of perfumers and flavourists pure undeca-1,3trans,5cis-triene and undeca-1,3 trans,5trans-triene, or convenient mixtures thereof.

Moreover, due to the nature of the compounds used as starting materials and reagents, the process of the invention is particularly advantageous both for technological and economical reasons.

The present invention relates further to a process for the preparation of phosphoranes of formula $$R^1-CH=CH-CH=CH^2-CH=PR_3 \qquad III$$

possessing a double bond of trans configuration at position 2 and wherein symbol R has the same meaning as that indicated for formula II, and $R^1$ represents an alkyl radical or a hydrogen atom, said process comprising:

a. adding a trialkyl- or triaryl-phosphine to a dihalo-compound of formula

IV $$R^1-\overset{Z}{\underset{|}{CH}}-CH=CH-CH_2-Z$$

wherein $R^1$ has the meaning above given and Z represents a halogen atom, and b. subsequently reacting the quaternary phosphonium salt thus obtained with at least 2 equivalents of a basic agent.

The conditions under which the reaction is effected are analogous to those commonly used in the art for carrying out the reactions of the Wittig type [H.O. House, op. cit.; R.F. Hudson, op. cit.].

Preferred basic agents include a strong base possessing a sterically hindered reactive centre such as for instance a tertiary alkoxide or a secondary amide, e.g. diisopropylamide or cyclohexylisopropylamide, of an alkali metal.

The novelty character of the above described process of the invention lies mainly on the particular original choice of the starting material. In fact, by operating by analogy with prior known methods, the man in the art would have tried to synthetize the phosphoranes of formula III, by adding a trialkyl- or triaryl-phosphine to a compound of formula

$$R^1-CH=CH-CH=CH^2-CH_2-Z \qquad V$$

possessing a double bond of trans configuration at position 2, followed by the treatment of the obtained quaternary phosphonium salt with one equivalent of basic agent. Such a synthetic method requires at first the preparation of the olefinic derivatives of formula V. This preparation is far from being simple and, in view of the high price of the starting material necessary, industrially uneconomical.

The invention equally relates to a process for the preparation of undeca-1,3trans,5cis-triene, said process comprising:

a. adding an organo-metallic compound of formula

$$CH_3-(CH_2)_4-CH\xrightarrow{cis}CH-ME \qquad VI$$

wherein Me represents an alkali metal or a radical comprising a transition metal, e.g. copper, and a univalent cation such as lithium⁺ for example, to a compound of formula

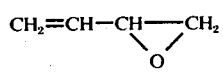

$$CH_2=CH-CH-CH_2 \qquad VII$$
$$\diagdown O \diagup$$

b. halogenating the thus obtained alcohols of formula

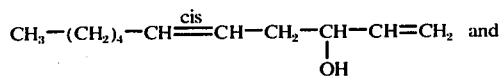
$$CH_3-(CH_2)_4-CH\xrightarrow{cis}CH-CH_2-CH-CH=CH_2 \text{ and}$$
$$\qquad\qquad\qquad\qquad\qquad\qquad\quad |$$
$$\qquad\qquad\qquad\qquad\qquad\qquad OH$$

of formula

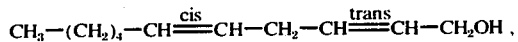
$$CH_3-(CH_2)_4-CH\xrightarrow{cis}CH-CH_2-CH\xrightarrow{trans}CH-CH_2OH,$$

and subsequently c. dehydrohalogenating the thus obtained halo-derivatives to give pure undeca-1,3trans,5cis-triene.

The addition of the organo-metallic compound of formula VI, which can be prepared in accordance with the methods described in J. Chem. Soc., 2078 (1951) and Helv. Chim. Acta, 54, 1939 (1971), to the compound of formula VII can be effected at a temperature lower than room temperature, preferably lower than 0° C according to the procedure described for analogous reactions [see e.g.: J. Am. Chem. Soc., 92, 4978 (1970); idem 93, 3047 (1971)].

The subsequent halogenation can be carried out in accordance with conventional techniques. Typically, suitable halogenating agents include gaseous chlorine, bromine or phosphoroustribromide in an inert solvent. Among the solvents which can be employed to this end, it is preferred to use an aliphatic or cycloaliphatic hydrocarbon, e.g. hexane or cyclohexane. Said halogenation is conducted at various temperatures, typically in the range from about 5° to 50° C. Suitable dehydrohalogenating agents include tertiary amines such as pyridine, quinoline or N,N-dimethylaniline. 1,5-Diazabicyclo[4.3.0]non-5-ene is preferred [cf. e.g.:L.F. Fieser and M. Fieser, Reagents for Organic Synthesis, J. Wiley & Sons, Inc., New York (1967)].

By the process of the invention it is now possible to directly prepare a composition of matter essentially consisting of undeca-1,3trans,5cis-triene.

A further object of the present invention is a perfuming or flavouring composition containing as an active ingredient a composition of matter essentially consisting of undeca-1,3trans,5cis-triene, undeca-1,3trans,5-trans-triene or a mixture thereof.

A still further object of this invention is a process for the preparation of perfumes or perfumed articles, which comprises adding thereto a composition of matter essentially consisting of undeca-1,3trans,5cis-triene, undeca-1,3trans,5trans-triene or a mixture thereof.

Finally, this invention relates to a foodstuff, beverage, animal feed, pharmaceutical preparaton or tobacco product having added thereto a small but effective amount of undeca-1,3trans,5cis-triene, undeca-1,3trans,5trans-triene or a mixture thereof.

The odoriferous properties of undeca-1,3cis,5cis-triene have been described in the scientific literature [Recherche, op. cit.] and, namely, in Swiss Pat. No. 496,084. Surprisingly it has now been discovered that not only compounds Ic and Id possess useful odoriferous properties, in contradistinction with the prior art teaching, but these compounds are equally suitable for developing, enhancing or modifying certain gustative notes. Particularly, by using the mentioned compounds or mixtures thereof it was possible to develop various notes such as fatty or green notes. This organoleptic characters are reminiscent of the taste of certain fruits, like citrus fruits, or vegetables.

Undeca-1,3trans,5cis-triene, undeca-1,3trans,5trans-triene and the mixtures thereof can be used on their own, or in compositions comprising one or more flavouring or odoriferous ingredients.

The proportions in which the said compounds are used in flavouring compositions can vary widely, depending upon the specific organoleptic effect it is desired to achieve and the nature of the materials to which they are added. Interesting flavouring effects can be achieved with amounts ranging from about 0.01 to 5 ppm, preferably from about 0.1 to 0.5 ppm, based on the total weight of the product flavoured.

When the said compounds are used or the preparation of artificial flavour compositions, they may typically constitute up to 30 % by weight of the composition.

Similarly, when used as perfuming ingredients, the proportion of the cited compounds in the perfume composition or perfumed product to which they are incorporated can vary over a wide range. Interesting odoriferous effects can be achieved with amounts ranging from about 0.1 to 2 % of the total weight of the composition.

In all cases, the ranges mentioned can be varied, in order to achieve specific odoriferous or flavouring effects.

Among the variety of compounds defined by the given formulae the following are new:
4-bromo-pent-2trans-en-1-yl triphenylphosphonium bromide,
penta-2trans,4-dien-1-yl triphenylphosphonium bromide,
penta-2trans,4-dien-1-yl triphenylphosphonium chloride, 3-hydroxy-undeca-1,5cis-diene,
undeca-2trans,5cis-dien-1-ol,
3-bromo-undeca-1,5cis-diene and
undeca-2trans,5cis-dien-1-yl bromide.

The invention is illustrated but not limited by the following examples, wherein the temperatures are indicated in degree centigrade and the abbreviations have the meaning common in the art.

EXAMPLE 1

Undeca-1,3trans,5cis-triene and
undeca-1,3trans,5trans-triene

A: NaH/DMSO 18.4 g (0.42 M) of a suspension of ca. 55 % of sodium hydride in oil, previously washed with 2 fractions of 25 ml each of pentane, were added to 420 ml of dimethylsulphoxide, whereupon the reaction mixture was heated under stirring to 75° during 45 min. then it was cooled to room temperature.

To this mixture 138 g (0.338 M) of penta-2trans,4-dien-1-yl triphenylphosphonium bromide were added during 20 min. under vigorous stirring and external cooling. There was thus obtained a dark red solution which, after having been left at 20° during 15 min., was mixed with 41 g (0.41 M) of n-hexanal under vigorous stirring during 25 min. The reaction mixture was further left at 25° for 45 min. then it was poured onto 400 ml of ice water, diluted with 200 ml of pentane, vigorously stirred and filtered on a support of Celite. The separated aqueous phase was extracted with pentane (200 ml) and the combined organic extracts dried over anhydrous magnesium sulphate and evaporated to give a residue (60 g) which, by purification by means of column chromatography (500 g of silica gel, Merck 0.05–0.2 mm; elution: hexane) gave 40 g of a colourless oil. By fractional distillation of this oil it was possible to obtain 35.6 g of a mixture of the desired products having b.p. 82°–4°/10 Torr (yield 70 % based on the weight of the phosphonium salt used as starting material).

The mixture thus obtained contained undeca-1,3trans,5cis-triene and undeca-1,3trans,5trans-triene in a weight ratio of 50:50.

Penta-2trans,4-dien-1-yl triphenylphosphonium bromide, used as starting material in the above given process, can be prepared as follows:

a. Penta-1,4-dien-3-ol 20 ml of a solution of vinyl bromide and 1 ml of methyl iodide were added under stirring to a suspension of 85 g (3.5 atom-g) of magnesium metal in 200 ml of tetrahydrofuran (THF) in the presence of some crystals of iodine. The reaction was carried out according to the procedure described in Org. Synth. Coll., Vol. 4, 258 (1963). After dilution of the reaction mixture with 800 ml of THF, 180 ml of the remaining vinyl bromide were added dropwise thereto. The obtained solution was then stirred during 2 h and cooled to −15°, whereupon 157 g (2.8 M) of acrolein in 400 ml of ether were added dropwise. The temperature of the mixture was then brought to 50° and stirring was continued for 1 h, then the whole was poured onto ice in the presence of a saturated aqueous solution of ammonium chloride.

After decantation and extraction of the aqueous layer with ether, the combined organic phases were dried over anhydrous magnesium sulphate and distilled to give 126 g of the desired alcohol.

B.p. 108°–116°/745 Torr $n_D^{17}$ = 1.4450 b. 1-Bromo-penta-2,4-diene

This product was prepared according to the method described in Ann. Chimie (Paris), 7, 445 (1962). By using 86 g (1.02 M) of penta-1,4-dien-3-ol 119 g of the corresponding bromo derivative were obtained; b.p. 58°/35 Torr.

c. Penta-2trans,5-dien-1-yl triphenylphosphonium bromide 104 g of the bromo derivative prepared in accordance with the method given under letter (b) hereinabove were added to a solution of 192 g (0.73 M) of triphenylphosphine in 1 lt of cyclohexane and the mixture was heated to reflux during 16 h. After cooling the desired product was collected by filtration and dried at 70° at reduced pressure (0.1 Torr) during 4 h. 232 g (80 %), m.p. 219°, were obtained.

NMR (CDCl$_3$ + traces of CD$_3$OD), 90 MHz: 4.58 (2H, $d+d$, $J_{P,H}$=16 cps, $J_2$=7 cps); 5.21 (2H, $m$); 5.54 (1H, $d+d+t$, $J_{PH}$=6 cps, $J_2$=14 cps, $J_3$=7 cps); 6.33 (2H, $m$); 7.82 (15 H, $m$) δ ppm.

by irradiation $^{31}$P : 4.58 (2H, $d$, J=7.5 cps); 5.58 (1H, $d+t$, $J_1$=15 cps, $J_2$=7.5 cps) δ ppm.

The corresponding quaternary phosphonium chloride can be prepared in an analogous way from 2-chloro-penta-2trans,4-diene, this latter compound being synthetized according to Ann. Chimie (Paris), 7. 445 (1962). The spectral data of penta-2trans,4-dien-1-yl triphenylphosphonium chloride were the following:

NMR (CDCl$_3$ + traces of CD$_3$OD), 90 MHz: 4.95 (2H, $d+d$, J= 7.01 cps, $J_{P,H}$=16 cps); 5.1 (2H, $m$); 5.54 (1H, $d+d+t$, $J_{P,H}$=6 cps, $J_2$=14 cps, $J_3$=7 cps); 6.3 (2H, $m$); 7.8 (15H, $m$) δ ppm M.p. 187°–9°.

Said phosphonium chloride can also be prepared from divinylcarbinol according to the following method:

3.25 g (39 mM) of divinylcarbinol were added dropwise and under stirring to a suspension of 10.5 g (40 mM) of triphenylphosphine in 20 ml of methanol containing 1.5 g of gaseous HCl. The addition was effected in 20 min. time at room temperature and the reaction mixture was then kept under stirring for 2 h, then set aside during 2 days. After filtration the clear filtrate was evaporated to dryness and the obtained solid residue crystallized in acetone to yield 2.55 g of the desired salt having m.p. 190°–2° together with 1.60 g of a fraction comprising the same compound having m.p. 187°–9° (yield 29 %).

B: BuLi/et$_2$O

To a suspension of 2.86 g (7 mM) of the phosphonium salt, prepared as indicated above in a finely divided powder form, in 20 ml of anhydrous ether, 5 ml (7 mM) of a 1.6 N solution of butyllithium in hexane were added under argon atmosphere. To the thus obtained red solution, 0.855 ml (7 mM) of hexanal, previously distilled, were added dropwise and the mixture was kept at reflux temperature during 1 h, whereupon it was poured into water. After extraction with pentane, washing with water of the separated organic phases, drying and evaporation there was obtained a residue which by fractional distillation in a bulb distillation apparatus gave 0.855 g (81 %) of a 33:66 mixture of undeca-1,3trans,5cis-triene and undeca-1,3trans,5-trans-triene. The analysis was conducted by vapour phase chromatography on a column of the type: Sp 1000, 4 mm × 2.5 m; 155°.

The spectral analysis of the pure isomers is shown by the enclosed figures. This analysis was carried out by means of the following apparatus:

NMR: Varian A-60 and Hitachi Perkin-Elmer R-20B for the measurements at 60 MHz; internal standard: $(CH_3)_4Si$; Bruker HFX-90/15 inch for the measurements at 90 MHz; internal standard: $(CH_3)_4Si$.

The abbreviations have the usual meaning, i.e.: $s$=singlet, $d$=doublet, $t$=triplet, $q$=quartet, $m$=multiplet.

IR: Perkin-Elmer No. 125; liquid film.

MS: Atlas CH 4; inlet temperature: 150°.

The analyses by means of vapour phase chromatography were carried out with a Carlo Erba GT type chromatograph; gas input: ca. 40 ml He/min.

Figure 6:
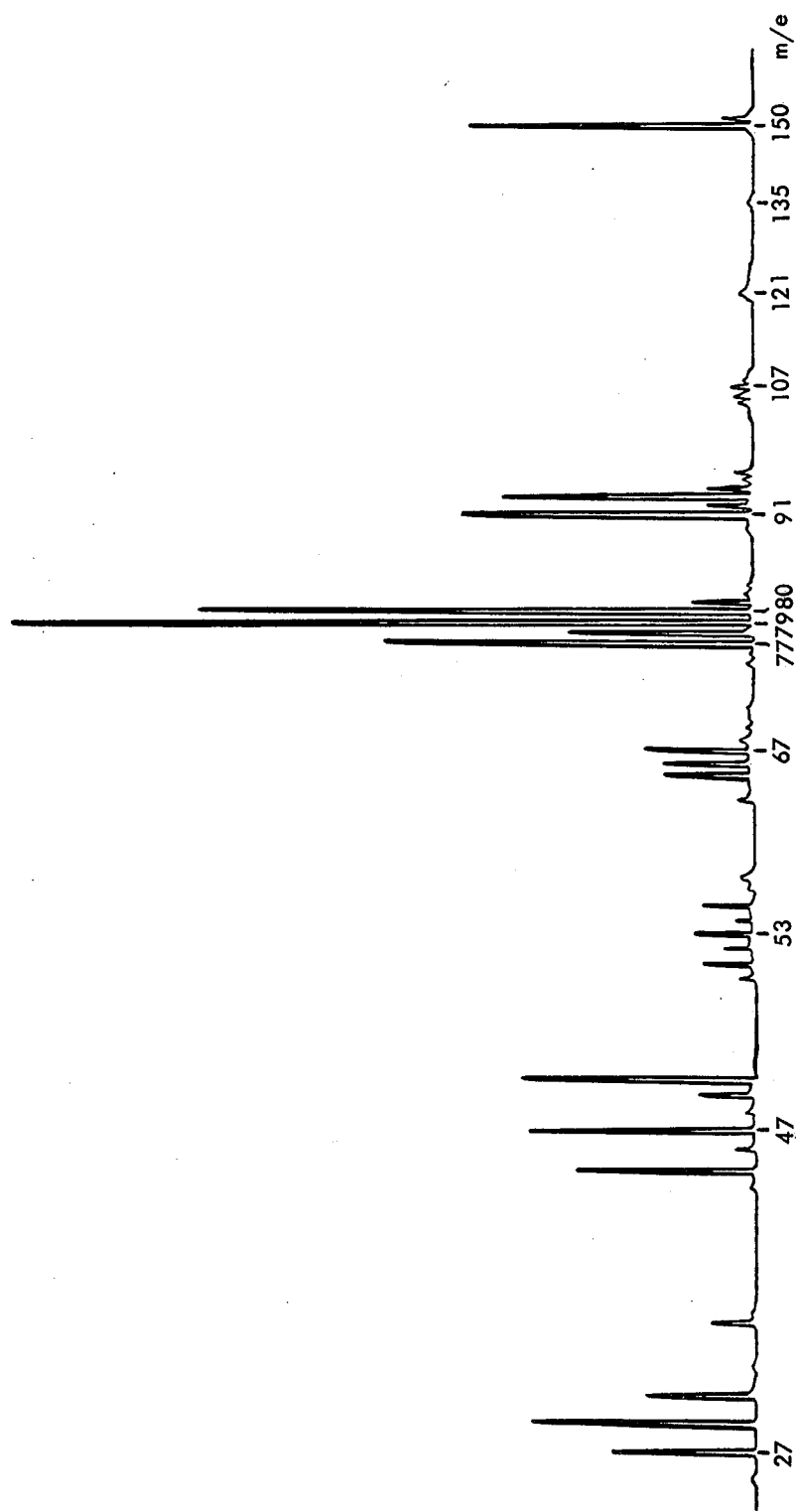

The NMR-spectra illustrated by FIGS. 6/1 and 6/4 were carried out by a 90 MHz instrument on a solution of the products under investigation in $CDCl_3$.

FIGS. 6/1, 6/2 and 6/3 represent the NMR, IR and MS-spectra of undeca-1,3trans,5cis-triene, respectively.

FIGS. 6/4, 6/5 and 6/6 represent the NMR, IR and MS-spectra of undeca-1,3trans,5trans-triene, respectively.

C: Potassium ter-butoxide/$Et_2O$

To a cooled suspension of 6.74 g (60 mM) of potassium ter-butoxide in 100 ml of anhydrous ether, 20.45 g (50 mM) of the phosphonium salt prepared according to paragraph A (c) were added in 15 min. in nitrogen atmosphere and under vigorous stirring. The reaction mixture was then heated to the reflux temperature and kept at this temperature during 3 h, then cooled to 17°. 5 g (50 mM) of hexanal in 35 ml of ether were then added to the mixture which was then refluxed during 1 h before having been cooled again to 20° and diluted with 100 ml of pentane. After filtration over Celite, washing of the clear filtrate with a saturated aqueous solution of $Na_4Cl$, drying over magnesium sulphate and evaporation, there was obtained a residue which was then treated with some ml of pentane and left 18 h at −20°. After a new filtration and evaporation of the clear filtrate there was obtained a residue which by fractional distillation in a bulb apparatus gave 5.1 g (68 %) of a mixture containing 40–60 parts by weight of undeca-1,3trans,5cis-triene and undeca-1,3trans,5-trans-triene, respectively.

B.p. 150°–220° (temperature of the oil bath)/11 Torr.

This product was previously stabilized with 10 mg of 3-ter-butyl-4-hydroxy-anisol.

EXAMPLE 2

Undeca-1,3trans,5cis-triene and undeca-1,3trans,5trans-triene

A. Potassium ter-butoxide/$Et_2O$ 24.5 g (0.05 M) of 4-bromo-pent-2trans-en-1-yl triphenylphosphonium bromide [which can be prepared according to the above given procedure] were slowly added to a suspension kept under stirring and in argon atmosphere of 13.5 g (0.12 M) of potassium ter-butoxide in 100 ml of anhydrous ether. The reaction mixture was kept under stirring overnight, whereupon 5 g (0.05 M) of hexanal in 35 ml of anhydrous ether were added thereto at a temperature of ca. 15°–25°. After having been left at 35° for 1 h, the mixture was cooled to room temperature, diluted with 130 ml of hexane, filtered over Celite and the clear filtrate, after washing with a saturated aqueous solution of $NH_4Cl$ and drying over magnesium sulphate, was kept 1 day at −20°. A subsequent purification was carried out by column chromatography by using 100 g of silica gel and elution with hexane. By distillation of the residue obtained on evaporation of the volatile portion of the eluate, 2.8 g (37 %) of a mixture comprising 44:56 parts by weight of hydrocarbons Ic and Id was obtained.

B. Potassium ter-butoxide/THF

By conducting the reaction in accordance with the method indicated in paragraph A above and using tetrahydrofuran (THF) instead of ether, a mixture comprising 44:56 parts by weight of hydrocarbons Ic and Id, respectively, was obtained with a yield of 52 %.

C. Potassium ter-butoxide/DMF

By carrying out the reacton in accordance with the method indicated in paragraph A above and by substituting dimethylfromamide (DMF) for ether, a mixture comprising 50:50 parts by weight of hydrocarbons Ic and Ic, respectively, was obtained with a yield of 60 %.

D. Lithium diisopropylamide/$Et_2O$ 67 ml (0.11 M) of a 1.6 N solution of butyllithium in hexane were treated at 0° with 11.1 g (0.11 M) of diisopropylamide, and the reaction mixture was kept at 0° under stirring during 30 min. To this reacton mixture there was then added 1 g of potassium ter-butoxide followed by 24.5 g (0.05 M) of 4-bromo-pent-2trans-en-1-yl triphenylphosphonium bromide and the mixture obtained was kept under stirring during 18 h at 23°, whereupon a solution of 5 g (0.05 M) of hexanal in 35 ml of anhydrous ether at 8°–15° was added thereto.

After having bee subjected to the same treatments as those described in paragraph A above, the reaction mixture gave with a 36 % yield a 34:66 parts by weight mixture of undeca-1,3trans,5cis-triene and undeca-1,3trans,5trans-triene.

4-Bromo-pent-2trans-en-1-yl triphenylphosphonium bromide, used as starting material in the above indicated method, can be prepared as follows:

a. 1,4-dibromo-pent-2cis-ene and 1,4-dibromo-pent-2trans-ene

The raw mixture of these compounds can be synthetized as described in Ann. Chimie (Paris) 10, [10] 377 (1928) and used directly for the subsequent reaction step.

b. 4-Bromo-pent-2trans-en-1-yl triphenylphosphonium bromide 910 g of the mixture of the dibromo derivatives obtained under letter a) hereinabove, were added under stirring at room temperature to a solution of 1050 g (4 M) of triphenylphoshine in 1360 ml of anhydrous toluene. After ca. 5 min. a slight warming up of the solution was observed concomittant with the formation of solid bromide. The reaction mixture was then left at room temperature for 5–8 days, then filtered. The solid cake was dried at first 4 h at 25°/12 Torr, then 9 h at 25°/0.1 Torr. The obtained product had m.p. 145° (yield: 68 % after 5 days reaction; 73 % after 8 days reaction). NMR ($CDCl_3$) at 90 MHz: 1.65 (3H, $d$, J=7 cps); 4.59 (2H, $d + d$, $J_{H,P}$=16 cps, $J_{H,H}$=7 cps); ca. 4.6 (1H, $m$); 5.66 (1H, $d + d + t$, $J_1$=15 cps, $J_{P,H}$≅6cps, $J_2$=7 cps); 6.17 (1H, $d+ d + d$, $J_1$=15 cps, $J_{P,H}$≅5 cps, $J_2$=8 cps); 7.85 (15 H, $m$) δ ppm.

EXAMPLE 3

Undeca-1,3trans,5cis-triene and undeca-1,3trans,5trans-triene

By reacting penta-1trans,3trans-dien-1-yl triphenylphosphonium chloride, in accordance to the reaction conditions indicated in the above example, with an amount of basic agent lower than that used in the course of the reaction described in the previous example (=½ of the quantity used in example 2), there is obtained with an analogous yield a mixture of the respective hydrocarbons.

The quaternary phosphonium salt used as starting material in the above described process can be prepared as follows:

A solution of 77 g (0.75 M) of 1-chloro-penta-2trans, 4-diene and 210 g (0.80 M) of triphenylphosphine in 500 ml of anhydrous toluene was heated under stirring at 100° for 48 h. The solid product thus formed was then separated by filtraton, washed with pentane and dried during 4 h at 50°/0.01 Torr. 152 g of the desired product having m.p. 191°–4° were obtained. By treating the mother liquors with 20 g of triphenylphosphine and heating the obtained solution for 12 h at 110°, 18 g of the same product having m.p. 189°–193° could be recovered (total yield 61 %).

NMR ($CCl_4$—$DMSOd_6$): 1.87 (3H, $d$, $J$=6.5 cps); 6–7.3 (4H, broad $m$); ca. 7.85 (15H, m) δ ppm.

EXAMPLE 4

Undeca-1,3trans,5cis-triene and undeca-1,3trans,5trans-triene

A. 1.68 g (10 mM) of a mixture (5:1 parts by weight) of undeca-1,5cis-dien-3ol and undeca-2,5cis-dien-1-ol, prepared according to the method described hereinbelow, in 5 ml of hexane were added dropwise under stirring to a mixture of 1.2 g of $PBr_3$ (4.2 mM) in 10 ml of hexane at 10°. The reaction mixture was then kept at room temperature overnight and diluted then with water. The separated organic phase was washed with water and with a 10 % aqueous solution of sodium bicarbonate, dried and concentrated. The residue thus obtained was subjected to a distillation by means of a bulb apparatus: 120°–130° (temperature of the oil bath) /10 Torr to give 1.5 g of undeca2trans, 5cis -dien-1-yl bromide 800 mg (3.5 mM) of this compound were then dissolved in 2 ml of dimethylsulphoxide and this solution was added dropwise to a stirred solution of 590 mg (385 mM) of 1,5-diaza-bicyclo[3.4.0]non-5-ene (DBN) in 10 ml of dimethylsulphoxide at 50°.

The reaction mixture was kept under stirring during 30 supplemental min. at 50°–55°, then extracted with pentane. The separated organic extracts, after the usual treatments of washing with water, drying over $MgSO_4$ and evaporation, gave a raw material which, on purification by means of column chromatography (20 g of silicagel 0.05–0.2 mm (Merck); eluant: hexane) gave 160 mg (30 %) of undeca-1,3trans, 5cis-triene having a purity of about 85 %.

B. 3.36 g (20 mM) of a 1:9 parts by weight mixture of undeca-1,5 cis-dien-3-ol and undeca-2,5cis-dien-1-ol, prepared according to the method described hereinbelow, and 340 mg of pyridine were added dropwise under stirring to a mixture of $PBr_3$ (0.715 ml; 7.5 mM) in 30 ml of benzene and 0.1 ml of pyridine at 10°.

The mixture was then heated at the reflux temperature during 30 min., whereupon it was poured into water and extracted with pentane. The separated organic phase was washed with a 10 % aqueous solution of sodium bicarbonate and with a saturated aqueous solution of sodium chloride, dried over $MgSO_4$ and concentrated.

A fractional distillation by means of a Vigreux column gave 3.41 g of undeca-2trans,5cis-dien-1-yl bromide. This product was dissolved in 10 ml of dimethylsulphoxide and the obtained solution was added dropwise under stirring to a solution kept at 50° of 2.5 g (16.5 mM) of 1,5-diaza-bicyclo [4.3.0]non-5-ene in 10 ml of dimethylsulphoxide. The reaction mixture was kept at 50°–60° under stirring for 30 min., then diluted with pentane, washed with water, dried over $MgSO_4$ and finally concentrated. On distillaton in a bulb apparatus at 115°–125° (temperature of the oil bath) /10 Torr, there were obtained 580 mg (26 %) of undeca-1,3trans,5cis-triene with a purity of 85 %.

The mixture of the alcohols used as starting material in the above described process can be prepared as follows:

a. 17.7 g (0.1 M) of 1-bromo-hept-1cis-ene were reacted at −10° with 1.4 g (0.2 M) of lithium metal containing 1.5 % of sodium in 60 ml of anhydrous ether. To the thus obtained mixture 7 g (0.1 M) of butadiene-monoepoxide in 10 ml of anhydrous ether were added at −10°. The mixture was kept at this temperature for 30 min. under stirring, then 2 h at +5° before pouring it into a 10 % ice solution of HCl.

By extracting with ether, washing the combined organic extracts with a saturated aqueous solution of NaCl, drying over $MgSO_4$ and concentration at reduced pressure, 12 g of the raw material were obtained. By distillation by means of a Widmer apparatus 9 g (53 %) of a product having b.p. 54°–59°/0.01 Torr were obtained. This product consisted of a 5:1 parts by weight mixture of the desired alcohols, namely:

3-hydroxy-undeca-1,5cis-diene and undeca-2trans,5-cis-dien-1-ol.

Spectral data:

3-hydroxy-undeca-1,5 cis-diene

NMR ($CCl_4$): 0.88 (3H, $t$, J=8 cps); ca. 1.3 (6H, $m$); 1.8–2.4 (4H, $m$); 2.85 (1H, $s$); 4.02 (1H, $d + t$, $J_1$=7 cps, $J_2$=7 cps); 4.8–5.5 (4H, $m$); 5.73 (1H, $d + d + d$, $J_1$=17 cps; $J_2$=11 cps; $J_3$=5 cps) δ ppm;

IR (film): 3380, 3090, 1645, 990, 920 and 730 $cm^{-1}$

MS: $M^+$ = 168 (0); m/e: 150 (0), 137 (0), 121 (0), 112 (19), 95 (1), 83 (16), 69 (29), 97 (100), 41 (35), 27 (27).

Undeca-2trans,5cis-dien-1-ol

NMR ($CCl_4$) : 0.88 (3H, $t$, J=8 cps); 1.3 (6H, m); 1,8–2 (2H, $m$); 2.75 (2H, $m$); 3.3 (1H, $s$); 3.8–4.2 (2H, $m$); 5.1–5.7 (4H, $m$) δ ppm;

IR ($CCl_4$): 3620, 1680, 995 and 970 $cm^{-1}$;

MS: $M^+$ = 168 (0); m/e: 150 (14), 135 (0), 124 (9), 107 (15), 93 (31), 79 (100), 67 (81), 55 (93), 41 (100), 29 (54).

b. The lithium derivative was prepared in accordance with the procedure indicated in paragraph (a) hereinabove by reacting 0.7 g (0.1 M) of lithium metal containing 1.5 % of sodium with 8.85 g (0.05 M) of 1-bromo-hept-1cis-ene and 40 ml of anhydrous ether. The thus obtained solution was added under stirring and in an argon atmosphere to a suspension of 4.76 g (25 mM) of copper iodide in 20 ml of anhydrous ether at −10°- −20°. The red solution obtained was then kept at −10° under stirring during 15 min. and then treated with 3.5 g of butadiene epoxide (0.05 M) in 10 ml of anhydrous ether at −10°. The reaction mixture was kept at this temperature during 1 h, then poured into a saturated aqueous solution of ammonium chloride in the presence of crushed ice, filtered over Celite, extracted with ether, washed, dried and concentrated to give 7 g of raw product. By fractional distillation through a Vigreux column, 5.2 g of a mixture having b.p. 77°–83°/0.8 Torr were obtained. This mixture comprised 7 % of 3-hydroxy-undeca1,5cis-diene and 83 % of undeca-2trans,5 cis-dien-1-ol as shown by the vapour phase chromatography on a CARBOWAX column at 5 %; temperature 180°.

EXAMPLE 5

Penta-2trans,4-dienylidene phosphorane 1.5 ml of dimethylsulphoxide-$d_6$ were added at about 80°–90° during 1 h to 192 mg (ca. 4 mM) of sodium hydride at 50 % in oil. This suspension of sodium hydride was preliminarily washed with 3 fractions of anhydrous ether, then dried under reduced pressure (12 Torr) at 80°.

Separately, a suspension of penta-2trans,4-dien-1-yl triphenylphosphonium bromide (1.636 g; 4 mM) in 2 ml of dimethylsulphoxide-$d_6$ was prepared and the sodium hydride reactant prepared above was added thereto. The reaction mixture was kept at room temperature under stirring during 1½ h, then the obtained red solution was centrifuged in order to obtain a clear liquid which was then subjected to a spectral analysis.

NMR (DMSO-$d_6$) at 90 MHz: 2.55 (standard band); 2.80 (ca. ½ H, $d+d$, $J_{P,H}$=22 cps, $J_1$=12 cps); 2.02 (1H, $d+d$, $J_1$=10 cps; $J_2$=2 cps); 2.27 (1H, $d+d$, $J_1$=17 cps; $J_2$=2 cps); 5.42 (1H, $d+d$, $J_1$=14 cps; $J_2$=11 cps); 5.7–6.4 (2H, m) δ ppm Irradiaton on $^{31}$P: 2.80 (ca. ½ H, $d$, J=12 cps); 5.7–6.4 (2H, m) δ ppm)

Irradiation on H$_3$ and H$_f$: 2.80 (ca. ½ H, d, $J_{P,H}$=22 cps); 2.02 (1H, $d$, J=2 cps); 2.27 (1H, $d$, J=2 cps) δ ppm.

EXAMPLE 6

100 ml of a syrup prepared by dissolving 1 kg of sucrose in 600 ml of water were flavoured with a 50:50 parts by weight mixture of undeca-1,3trans,5cis-triene and undeca-1,3trans,5trans-triene ind the proportion of 0.5 ppm by weight of the flavouring ingredient based on the total weight of the flavoured material (A).

In an analogous way a salt solution containing 0.5 % of NaCl was flavoured (B).

Foodstuffs A and B thus prepared were tasted by a panel of flavour experts who defined their taste and aroma as possessing a note:
A. fatty, green reminiscent of the characters of certain vegetables or citrus fruits, and
B. of the type "heated fat".

EXAMPLE 7

Two flavouring compositions were prepared by admixing the following ingredients (parts by weight):

| | A (test) | B (control) |
|---|---|---|
| Mandarine essential oil | 300 | 300 |
| 50:50 parts by weight mixture of undeca-1,3 trans, 5 cis-triene and undeca-1,3 trans,5 trans-triene at 1°/oo in 95% ethanol | 30 | — |
| 95% ethanol | 670 | 700 |
| Total | 1000 | 1000 |

The two compositions were added to the hereinbelow indicated foodstuff in the proportion of 60 g of composition per 100 kg of foodstuff:

Toffee: 100 ml of sugar syrup (obtained by dissolving 1 kg of sucrose in 600 ml of water) and 20 g of glucose were mixed and slowly heated to 145°. The flavour was added to the mass and the whole cooled to harden.

A sample of the finished foodstuff was tasted by a panel of flavour experts who declared that the foodstuff flavoured by A possessed by comparison with the foodstuff flavoured by B a greener, fattier and more woody like note, while possessing a more distinct character of mandarine.

EXAMPLE 8

Fragrance composition of the "pine" type for foam-bath preparation

A base perfume composition of the pine type was prepared by mixing the following ingredients (parts by weight):

| | |
|---|---|
| Isobornyl acetate | 500 |
| Siberia pine oil | 200 |
| Terpenyl acetate | 100 |
| Methyl-nonylacetaldehyde 10%* | 100 |
| Cedar-leaf oil | 30 |
| Ambrette musc | 20 |
| Lavandin oil | 20 |
| Dodecanal 10%* | 10 |
| Coumarin | 10 |
| cis-Hex-2-enyl formate 1%* | 10 |
| Total | 1000 |

*in diethyl phthalate

By adding to 980 g of the above composition 20 g of a 10 % solution of a 50:50 parts by weight mixture of undeca-1,3trans,5cis-triene and undeca-1,3trans,5-trans-triene in diethyl phthalate, it was obtained a new composition, the fragrance of which was richer and more harmonious than that of the base composition. This new composition presented moreover a well defined note of galbanum oil.

What is claimed is:

1. Process for the preparation of undeca-1,3trans,5-cis-triene and/or undeca-1,3trans,5trans-triene, which comprises reacting a quaternary phosphonium salt of formula

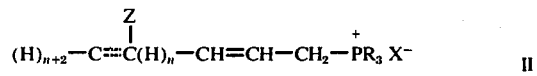

II wherein symbol R represents an aliphatic, cycloaliphatic or aromatic radical and X represents a halogen atom, such as chlorine, bromine or iodine, or a group such as BF$_4$ or ClO$_4$, and wherein:
 a. indedx n stands for 1, Z represents a halogen atom and the dotted lines define a single bond; or
 b. index n stands for zero, Z represents a hydrogen atom and the dotted lines define a double bond,
with hexanal, and subsequently separating the pure geometrical isomers.

2. Process according to claim 1, wherein the compound of formula II is 4-bromo-pent-2trans-en-1-yl triphenylphosphonium bromide.

3. Process according to claim 1, wherein the compound of formula II is penta-2trans,4-dien-1-yl triphenylphosphonium bromide or chloride.

4. Process according to claim 1, wherein the reaction is carried out in the presence of a basic agent.

5. Process according to claim 4, wherein the basic agent is an alkali metal hydride or alkoxide, an alkyl or aryl derivative of an alkali metal or a mixed basic agent.

6. Process according to claim 5, wherein the basic agent is a member selected from the group consisting of lithium hydride, sodium hydride, potassium ter-butoxide, butyl-lithium or lithium diisopropylamide.

7. Process according to claim 4, wherein the basic agent is a strong base possessing a sterically hindered reactive centre.

8. Process according to claim 7, wherein the base is an alkali metal ter-alkoxide or an alkali metal secondary amide.

9. Process according to claim 1, wherein the reaction is carried out in diethyl ether, dimethoxy-ethane, tetrahydrofuran or dimethylformamide.

10. Process according to claim 1 wherein the pure geometrical isomers are separated one from the other by means of preparative vapour phase chromatography.

* * * * *

UNITED STATES PATENT AND TRADEMARK OFFICE
CERTIFICATE OF CORRECTION

PATENT NO. : 4,014,951
DATED : March 29, 1977
INVENTOR(S) : Ferdinand Naf et al.

It is certified that error appears in the above-identified patent and that said Letters Patent are hereby corrected as shown below:

Column 2, line 15, "thir" should be --their--

Column 5, Formula (1), "PPh" last occurrence, should be --$PPh_3$--

Column 8, line 47, "or" should be --for--

Column 12, line 24, "Ic and Ic" should be --Ic and Id--

Column 12, line 56, "triphenylphoshine" should be --triphenylphosphine--

Column 15, line 40, "$H_3$", should be --$H_e$--

Column 16, line 33, "musc", should be --musk--

Column 16, line 63, "indedx", should be --index--

Signed and Sealed this

Fourth Day of October 1977

[SEAL]

Attest:

RUTH C. MASON
Attesting Officer

LUTRELLE F. PARKER
Acting Commissioner of Patents and Trademarks